(12) United States Patent
Tsujino et al.

(10) Patent No.: US 6,293,913 B1
(45) Date of Patent: Sep. 25, 2001

(54) DOPPLER ULTRASONIC DIAGNOSIS APPARATUS

(75) Inventors: Hiroyuki Tsujino, Cleveland, OH (US); Takuya Sasaki, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/501,240

(22) Filed: Feb. 10, 2000

(30) Foreign Application Priority Data

Feb. 10, 1999 (JP) ................................................. 11-032745

(51) Int. Cl.$^7$ ........................................................ A61B 8/12
(52) U.S. Cl. ................................................ 600/450; 600/453
(58) Field of Search .................................... 600/437, 407, 600/440–447, 449, 450, 453–457, 485, 483; 73/625, 626; 367/7, 11, 130

(56) References Cited

U.S. PATENT DOCUMENTS

| | | | |
|---|---|---|---|
| 3,813,654 | * | 5/1974 | Clifton et al. ........................ 600/453 |
| 4,086,917 | * | 5/1978 | Burks et al. ......................... 600/453 |
| 5,425,365 | * | 6/1995 | Iinuma ................................. 600/441 |
| 5,690,111 | * | 11/1997 | Tsujino ................................ 600/440 |
| 5,701,897 | * | 12/1997 | Sano ................................... 600/455 |
| 5,785,654 | * | 7/1998 | Iinuma et al. ....................... 600/441 |
| 6,050,948 | | 4/2000 | Sasaki et al. . |

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

A Doppler ultrasonic diagnosis apparatus is characterized by: transmitting ultrasonic beams between diagnosis sites including a motion fluid in the object's body; receiving its ultrasonic echoes; generating a display image of a Doppler spectrum consisting of the spectrum every moment of a Doppler signal in an ultrasonic Doppler effect due to a motion of a motion fluid based on the ultrasonic echoes; selecting a Doppler spectrum targeted for measurement from this generated display image; automatically recognizing the heart beat range in the selected Doppler spectrum; and measuring an index value for Doppler diagnosis every heart beat range thus recognized. With this characteristics, this apparatus simplifies manual operation during measurement using the Doppler spectrum, and reduces the operation quantity and diagnosis time required for measurement.

11 Claims, 8 Drawing Sheets

DOPPLER ULTRASONIC DIAGNOSIS APPARATUS

BACKGROUND OF THE INVENTION

The present invention relates to a Doppler ultrasonic diagnosis apparatus for diagnosing motion fluid such as blood flow in vivo by utilizing a Doppler effect of ultrasonic waves.

Conventionally, it is known that a Doppler ultrasonic diagnosis apparatus uses an ultrasonic pulse Doppler technique and an ultrasonic pulse reflection technique, thereby acquiring a tomographic Image (a monochrome mode image) and blood flow information by a single ultrasonic probe and displaying at least the blood flow information in real time.

In this Doppler ultrasonic diagnosis apparatus, in recent years, a frequency that meets conditions for setting a maximum blood flow velocity or gravity blood flow velocity and the like on a Doppler frequency spectrum based on the acquired blood flow information is traced in real time or after freeze operation. Then, characteristics velocities such as average flow velocity value, maximum flow velocity, minimum flow velocity is obtained from a time change curve of a blood flow velocity obtained from this trace processing result. There is proposed a method for calculating and diagnosing various physical quantities (hereinafter, referred to as "index (index value)" such as PSV (Peak Systolic Velocity) or EDV (End Diagnostic Velocity) using this velocity. In this case, in a course up to performing diagnosis from the acquired blood flow information, frequency trading is automatically performed, thereby making it possible to significantly reduce the operation quantity and operation time of an operator in comparison with a case when that tracing is manually performed.

However, in the above mentioned conventional Doppler ultrasonic diagnosis apparatus, in the case where index is measured and diagnosed by employing the trace results of the frequency that meets the setting conditions on the Doppler spectrum, the following problem will occur.

That is, in the case of the conventional apparatus, although frequency tracing itself is automatically performed, an operation for selecting a spectrum targeted for diagnosis by reproducing a freeze memory or an operation for determining a heart beat targeted for measurement by specifying a time range (ROI: region of interest) of the spectrum targeted for mesurement must still be manually performed. Among them, in particular, specifying ROI requires very strict position specifying work, and thus, operation Is prone to be difficult. In addition to this, In the case of tracing after freezing, an operation for instructing the start of tracing is required, or in the case of real-time tracing, when the tracing result is set to non-display, an operation for specifying the start of display is required. Therefore, in view of the operation quantity and operation time of the entire diagnosis, an operation portion to be performed manually is still considerably large.

On the other hand, in the case where blood flow information is traced in real time, index calculation is performed in real time based on the trace processing result. However, there is a problem that it is very difficult for the operator to monitor the calculated index in real time. Moreover, it is impossible to calculate the time change of the index calculated in real time and reflect it on an freeze operation or the like.

SUMMARY Of THE INVENTION

The present invention has been achieved in view of such conventional problem. It is a first object of the present invention to simplify manual operation during measurement using Doppler spectrum and reduce the operation quantity and diagnosis time required for measurement.

In addition, it is a second object of the present invention to comprehensively and simply perform an operation for selecting a Doppler spectrum targeted for diagnosis or an operation for specifying an ROI on the spectrum and reduce the operation quantity and diagnosis time required for diagnosis.

Further, it is a third object of the present invention to perform an operation for replacing the specified ROI and reduce the operation quantity and diagnosis time required for diagnosis by operating the data targeted for diagnosis according to the ROI.

Furthermore, it is another object of the present invention to calculate an index in real time in the case where frequency tracing is performed in real time, and at the same time, calculate the time change In real time and easily perform monitoring, provide the monitoring results as operational information and measurement values, and display all of these processing results on the screen and easily check them.

To achieve the aforementioned object, and in particular, reduce the operation quantity and operation time effectively, the present invention is directed to an arrangement comprising means for comparing a time position between a position of a characteristic point (time position such as PSV and EDV) reflecting a heart beat on a Doppler spectrum and a ROI position; means for identifying a heart beat on the Doppler spectrum which is the closest to the POI position based on the comparison results; and means for displaying the heart beat thus identified and the ROI position on the screen.

In this arrangement, it is possible to apply an art proposed in Japanese Patent Application Laid-open No. 11-033024 (an art designed by one of the Inventors), i.e., means for automatically detecting a velocity value measured by employing the trace results of frequency that meets predetermined conditions on the Doppler spectrum, respectively at a plurality of positions (times) that meets predetermined conditions, thereby identifying a heart beat.

With these means, in a course up to performing diagnosis from the acquired blood flow information, an operation for specifying a ROI position in advance, thereby reproducing an image memory and selecting a spectrum targeted for diagnosis is compatible with an operation for determining a heart beat targeted for measurement, thus making it possible to reduce the operation quantity and operation time.

Together with this, in order to achieve the foregoing object, the present invention is directed to an arrangement comprising means for calculating a time change of an index value (index) calculated in real time; means for monitoring the time change of the index value thus calculated; and means for displaying the above index value and the related time change and monitor results in real time.

In the above arrangement, there can be further provided means for monitoring operation on an operating panel; and means for generating a command signal at another circuit according to the operation on the operating panel.

With these means, in the case of real-time tracing, it is possible to calculate the time change of the index value calculated in real time and provide the calculation result as operational information and measurement value.

The Doppler ultrasonic diagnosis apparatus according to the present invention has been completed based on the above technical idea.

That is, the Doppler ultrasonic diagnosis apparatus according to the present invention is featured by comprising transmitting and receiving means for transmitting ultrasonic beams between a diagnosis site including a motion fluid in the object's body and receiving the ultrasonic echoes; display image generating means for measuring the spectrum every moment of Doppler signals in the ultrasonic Doppler effect due to the motion of the motion fluid based on the ultrasonic echoes received by the transmitting and receiving means, thereby generating the Doppler spectrum display image; selecting means for selecting a Doppler spectrum targeted for measurement from the display image generated by this display image generating means; heart beat recognizing means for automatically recognizing a heart beat range in the Doppler spectrum selected by this selecting means; and measurement means for measuring an Index value for Doppler diagnosis every heart beat range recognized by this heart beat recognizing means.

The heart beat recognizing means can be means for automatically recognizing a heart beat range based on information on a characteristic point in a time change of frequency that meets a predetermined condition in the Doppler spectrum selected by the selecting means.

The heart beat recognizing means can be means for comparing a position of the ROI preset on a display image generated by the display image generating means, thereby automatically recognizing the heart beat range having parameters within the range of ROI based on the comparison results.

The heart beat recognizing means can be means for scrolling the Doppler spectrum according to the ROI preset on the display image, thereby automatically realizing the heart beat range having the characteristic point within the range of the ROI.

The measuring means can comprise detecting means for detecting a frequency that meets a predetermined condition preset from the Doppler spectrum targeted for measurement; extracting means for extracting the position of the characteristic point and its value based on a time change of the frequency detected by this detecting means; heart beat identifying means for identifying the heart beat range based on the position of the characteristic point and its value extracted by this extracting means; and calculating means for calculating an index value for Doppler diagnosis every heart beat range identified by this heart beat identifying means.

The present invention can further provide means for measuring the time change of the index value calculated by the calculating means every heart beat.

The heart beat recognizing means can comprise electrocardiogram acquiring means for synchronizing with transmission and reception of the ultrasonic beams to the object's body with the transmitting and receiving means, thereby acquiring an electrocardiogram of the object's body; and means for automatically recognizing the heart beat range of the Doppler spectrum by employing the electrocardiogram acquired by this electrocardiogram acquiring means.

The present invention can comprise extracting means for automatically tracing a frequency that meets a predetermined condition of a Doppler spectrum from a display image generated by the display image generating means, thereby extracting the position of the characteristic point and its value for identifying a heart beat based on the time change of that frequency; and measuring means for calculating a diagnosis index value based on the position of the characteristic point and its value extracted by this extracting means, thereby measuring the time change of the index value.

The present invention can further provide means for graphically representing the measurement results obtained by the measuring means on the display image.

The Doppler ultrasonic diagnosis apparatus according to the present invention can comprise transmitting and receiving means for transmitting ultrasonic beams between diagnostic sites including a motion fluid in the object's body and receiving its ultrasonic echoes; display image generating means for measuring the spectrum every moment of Doppler signals in the ultrasonic Doppler effect due to the motion of the motion fluid based on the ultrasonic echoes received by this transmitting and receiving means, thereby generating a display image of the Doppler spectrum; extracting means for automatically tracing a frequency that meets a predetermined condition for the Doppler spectrum from a display image generated by this display image generating means, thereby extracting the position of the characteristic point and its value for identifying the heart beat based on the time change of the frequency extracted by this extracting means; and measuring means for calculating the diagnosis index value based on the position of the characteristic point and its value extracted by this extracting means, thereby measuring the time change of the index value.

The present invention can further provide means for graphically representing the measurement results obtained by the measuring means on the display image.

According to the present invention, in a course up to performing diagnosis from the acquired blood flow information, unlike a conventional apparatus, even if a position of a target to be measured is not strictly specified by ROI operation displayed on the screen, a heart beat can be identified easily and speedily. Thus, the entire operation quantity and operation time can be significantly reduced.

In addition, according to the present invention, an operation for specifying a ROI position in advance, thereby reproducing an image memory and selecting a spectrum targeted for diagnosis is compatible with an operation for determining a heart beat targeted for measurement, thus making it possible to reduce the operation quantity and operation time.

Further, according to the present invention, in the case of real-time tracing, a time change of an index calculated in real time is calculated, making it possible to the calculation result as operational information and measurement values.

BRIEF DESCRIPTION OF THE DRAWINGS

The accompanying drawing which are incorporated in and constitute a part of this specification, illustrate embodiments of the present invention and, together with the description, serve to explain the principles of the present invention; in which:

FIG. 3A and FIG. 3B are schematic flowcharts illustrating operation and calculating procedures in comparison with a conventional example, wherein

DESCRIPTION OF THE PREFERRED EMBODIMENTS

Hereinafter, embodiments of the Doppler ultrasonic diagnosis apparatus according to the present invention will be described with reference to the accompanying drawings.

Figure 1:
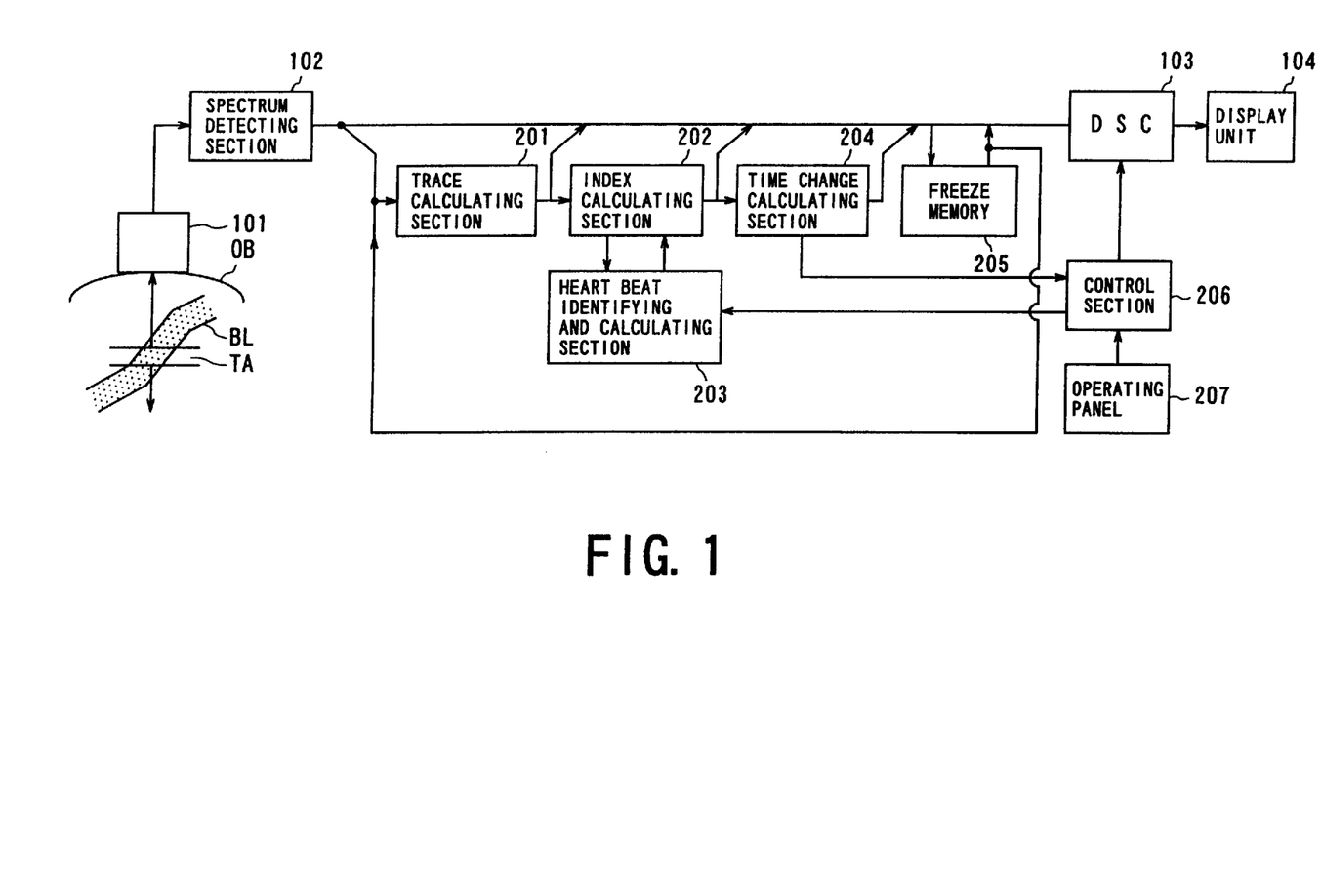
FIG. 1 is a schematic block diagram depicting an embodiment of a Doppler ultrasonic diagnosis apparatus according to the present invention.

The Doppler ultrasonic diagnosis apparatus shown In FIG. 1 comprises an ultrasonic probe having an ultrasonic oscillator 101 for transmitting and receiving ultrasonic waves between diagnosis sites TA including blood vessel BL in the object's body OB; a spectrum detector 102 for calculating a frequency spectrum based on Doppler information due to the ultrasonic Doppler effect in vivo reflected on the ultrasonic echoes received by the ultrasonic oscillator 101; a DSC 103 for converting the frequency spectrum from this detector 102 into image data; and a display unit 104 for displaying the image data from this DSC 103 as a Doppler image indicative of the time change of the Doppler spectrum.

In addition, in order to execute various measurements based on a frequency spectrum, this Doppler ultrasonic diagnosis apparatus comprises various calculating sections between a spectrum detector 102 and a DSC 103, i.e., a trace calculating section 201, an index calculating section 202, a heart beat identifying and calculation section 203, and a time change calculating section 204; a freeze memory 205 for holding various data for scroll reproduction during freeze operation; a control section 206 for controlling operation of various calculating sections or the like; and an operating panel 207 for the operator to input various commands.

The trace calculating section 201 is structured of having a computer executing a program basyed on a preset algorithm, for example. By this computer processing, a frequency that meets the conditions for setting maximum frequency trace or gravity frequency is traced for data on the Doppler spectrum from the spectrum detector 102 or data on the Doppler spectrum read out from the freeze memory 205 after freeze, and the trace processing results are outputted to the index calculating section 202, DSC 103, and freeze memory 205 as required, respectively.

The index calculating section 201 is structured of having a computer for executing a program based on present algorithms, for example. By this computer processing, information concerning a variety of characteristic velocities (time position of the characteristic point of PSV and EDV and its value) is detected for the trace processing results of the frequency from the trace calculating section 201, and the information is outputted to the heart beat identifying and calculating section 203. On the other hand, various indexes (index values) such as PSV and EDC for each heart beat are calculated for the heart beat identification results outputted from this heart beat identifying and calculating section 203 and the information concerning a variety of the characteristic velocity, and trace processing results, and these indexes are outputted to the time change calculating section 204, DSC 103, and freeze memory 205 as required, respectively.

Figure 2:
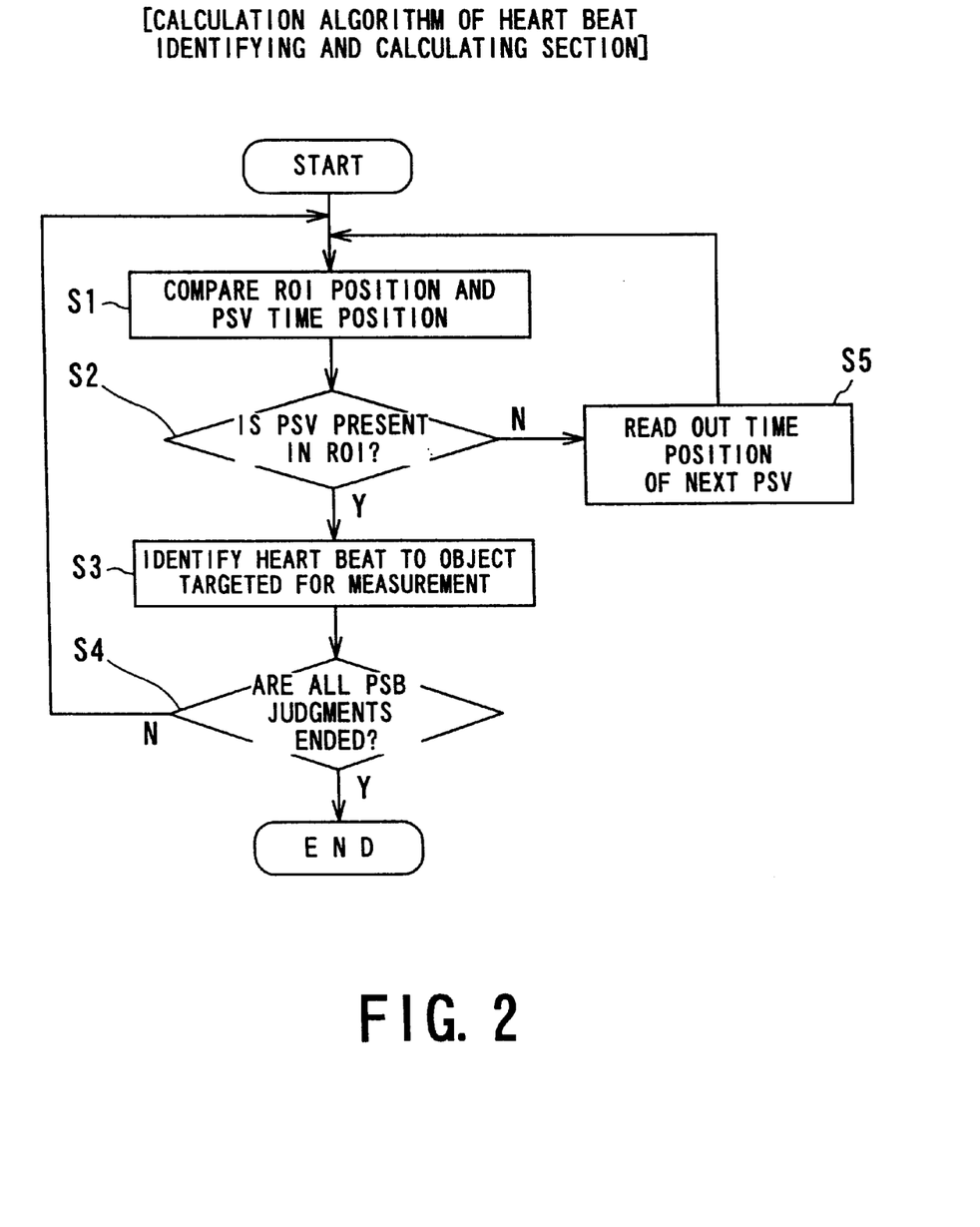
FIG. 2 is a schematic flowchart showing processing at a heart beat identification portion according to the present invention.

The heart beat identifying and calculating section 203 is structured of having a computer for executing a program based on a preset algorithm, for example. By this computer, processing shown in FIG. 2, for example, is performed. In this computer processing, first, the time position of PSV of the data calculated by the index calculating section 202 is compared with the ROI specified position captured by the operator's operation from the operating panel via the control section 206 (step S1). By this comparison, it is judged whether or not PSV is present inside of the ROI (step S2). By this judgment, In the case of YES (In the case where the PSV is present inside of the ROI), one heart beat including the PSV is identified as an object targeted for measurement (step S3). Conversely, in the case of NO (in the case where the PSV is not present inside of the ROI), the time position of the next PSV is read out in step S5, and processing returns to step S1. A series of processes in these steps S1 to S3 is repeatedly performed until all PSV have terminated in step S4.

The time change calculating section 204 is structured of having a computer for executing a program based on a preset algorithm, for example. By this computer processing, an average and standard deviation or the like is calculated for the PSV, EDV or the like of each heart beat from the index calculating section 6 in real time, and the calculation results are outputted to the DSC 103 and the freeze memory 205 as required, respectively.

The freeze memory 205 writes Doppler spectrum data from the spectrum detector 102, the trace results of the trace calculating section 201 as required, and various data on a variety of characteristic velocities detected by the index calculating section 202. Then, the memory 205 supplies various data written into the DSC 103 by the operator's reproduction instructing command after freeze operation, and supplies the data on the Doppler spectrum to the trace calculating section 201.

The control section 206 outputs an instructing signal from the operating panel 207 or a freeze instructing signal or the like based on the output results of various calculating sections such as time change calculating section 204. In addition, it outputs the calculation position (ROI) signal on the Doppler spectrum displayed on the display unit 104 to the heart beat identifying and calculating section 203, and outputs a reproduction instructing signal of the freeze memory 205. A predetermined marker corresponding to the ROI signal can be displayed on the display unit 104.

The operating panel 207 comprises a trackball or a keyboard where the operator can make an operation arbitrarily, v'herein an Instructing signal inputted by the operator's operation can be outputted to the control section 206.

Figure 3A:
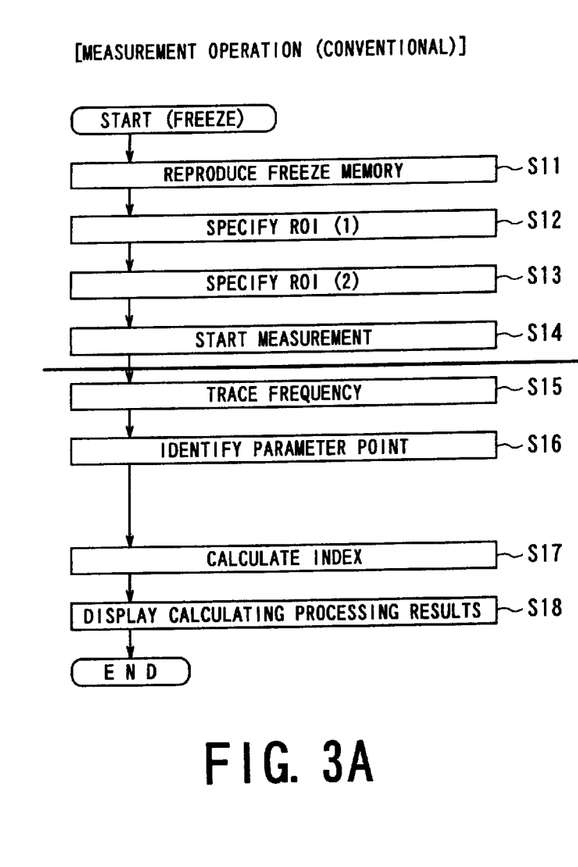
FIG. 3A is a view illustrating a case of conventional measurement.
Figure 3B:
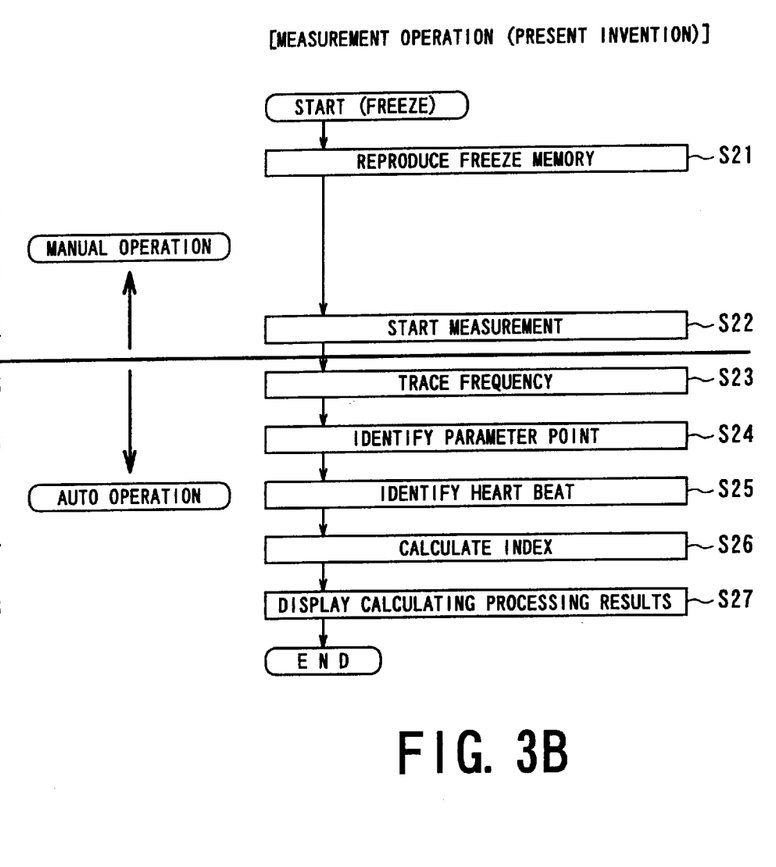
FIG. 3B is a view Illustrating a case of the mesurement according to the present invention.

Hereinafter, an entire operation of this embodiment will be described with reference to FIG. 3 to FIG. 6. FIG. 3A and FIG. 3B are illustrative view comparing the convention measurement operation and the measurement operation of the present invention.

First, in the conventional measurement operation, as shown in FIG. 3A, the freeze memory 205 is reproduced after freeze, whereby the Doppler spectrum targeted for diagnosis is displayed on the display unit 104 (step S11). An object targeted for measurement is set by specifying the ROI through the operators operation (ROI specifications (1) and (2) in the figure specify the upper and lower limits of the time range) while the operator sees the Doppler spectrum on this display unit 104 (steps S12 and S13), and measurement is started (step S14). Operations from the steps S11 to S14 are manually performed.

Hereinafter, the tracing of the frequency that meets a predetermined condition during auto calculating processing (step S15), identification of parameter points (step S16), and index calculation (step S17) are sequentially executed, these various calculating processing results are displayed (step S18), and measurement operation terminates.

Therefore, in the case where the blood flow velocity, average flow velocity or the like is measured by the conventional measuring instrument using the spectrum Doppler waveforms, the ROI indicative of the measurement range is specified (in general, the ROI is specified by one heart beat). Thereafter, in order to perform automatic measurement targeted for the waveforms in the ROI, a three-step operation is required, i.e., 1) moving the targeted Doppler spectrum before measurement into the display region (waveform movement by scrolling the frame memory); 2) Specifying ROI (specifying two points, i.e., the upper and lower limits of the measurement range); and 3) initiating measurement (including trace).

In contrast, in measurement operation of the present invention, as shown in FIG. 3B, the freeze memory 205 is reproduced after freeze in step S21, whereby when the Doppler spectrum targeted for diagnosis is displayed on the display unit 104, specifying the ROI terminates at this time. This operation will be described with reference to FIG. 4 to FIG. 6.

First, the freeze memory 205 has a time storage capacity several times as large as the display time range of the display unit 104, displays the past Doppler spectrum in reproduction after freeze, and can implement measurement operation on this Doppler spectrum.

Figure 4:
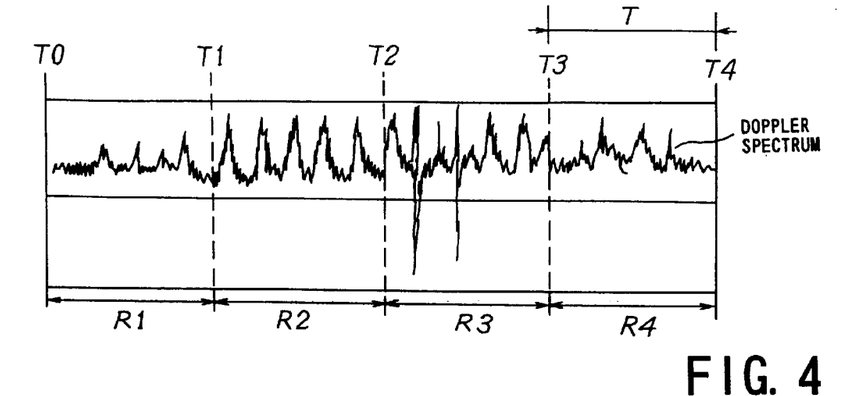
FIG. 4 is a schematic graph depicting a display example of the Doppler spectrum immediately after freeze operation.

FIG. 4 schematically depicts the Doppler spectrum immediately after freeze recorded in the freeze memory 205 in a form in which the spectrum is displayed on the display unit 104. The state of the Doppler spectrum from time T0 to T4 obtained when freeze occurs at time T4 is displayed by dividing it into regions R1 to R4 at equal time intervals T. In this Doppler spectrum, a time-based stable pattern in region R2, a time-based unstable pattern in region R1 and R4, and a pattern in which a clutter component due to the relatively slow movement in vivo such as blood vessel is mixed in region R3 are schematically expressed, respectively.

In the case where such Doppler spectrum is obtained, there is a possibility that the operator selects a time-based stable pattern as an object targeted for measurement, i.e., region R2. Namely, if the displayable time range of the display unit 104 is time T, the freeze memory 205 is reproduced by time corresponding to 2T by the operator's operation, and the region R2 can be displayed as an object targeted for diagnosis.

Figure 5A:
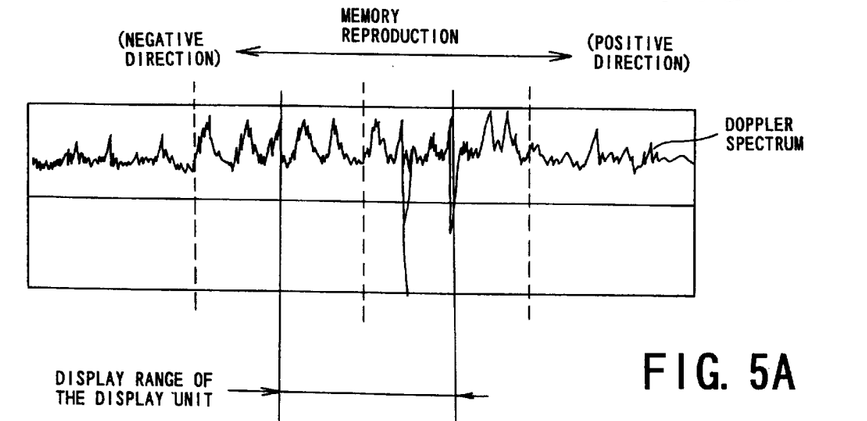
FIG. 5A and FIG. 5B are schematic graphs illustrating a relationship between a freeze memory storage range and a display range of a display unit according to the present invention.
Figure 5B:
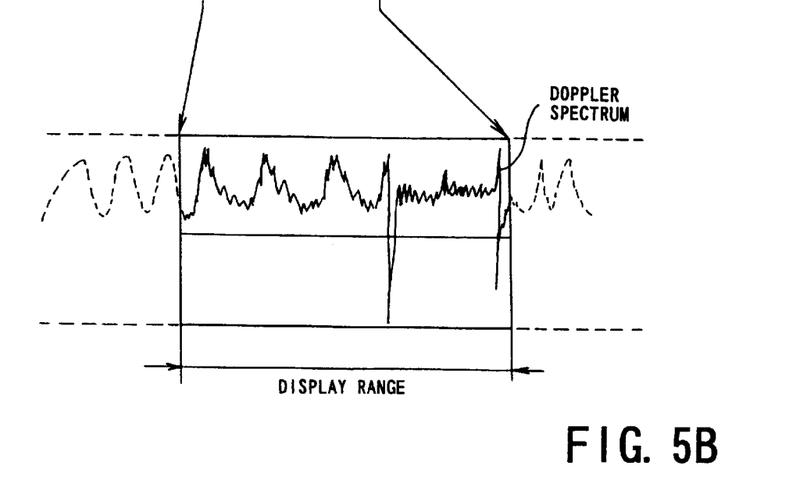

FIG. 5A and 5B illustrate a relationship between the storage range of the freeze memory 205 and the display range of the display unit 104. In this case, on the screen of the display unit 104, the Doppler spectrum out of the display range is scrolled In positive direction (right direction in the figure). Such operation is generally performed in Doppler diagnosis expect in the case freeze is performed at time T2.

Figure 6:
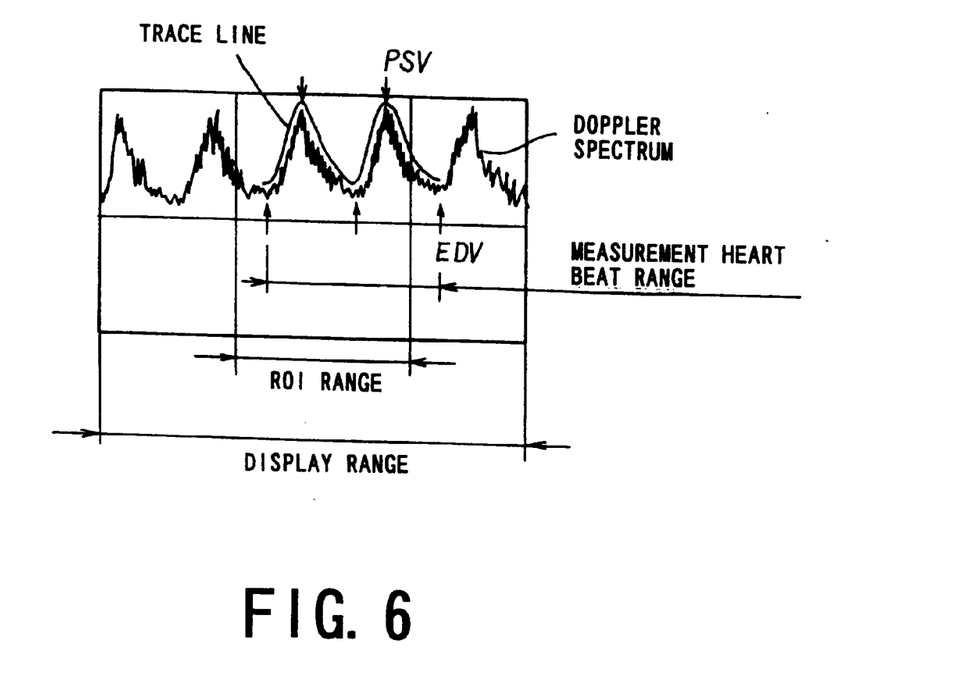
FIG. 6 is a schematic graph depicting a display example of trace results relevant to a target heart beat, PSV, and EDV according to the present invention.

FIG. 6 illustrates a relationship between the ROI and Doppler spectrum in a state in which the region R2 is displayed by the above mentioned operation. In this case, the ROI time range is set with a time width corresponding to the measurement heart beat (two heart beats in the figure). When the frame memory 205 is reproduced so that the PSV at a heart beat targeted for measurement enters this ROI, the heart beat including this PSV is identified as an object targeted for measurement by processing of the heart beat identifying and calculating section 203 (refer to FIG. 2). That is, ROI specification is completed at a time when frame memory reproduction has terminated during processing in the above mentioned step S21.

Thus, when ROI specification is completed by frame memory reproduction, the start of measurement is instructed in step S22. This instruction is performed by the operator generating a command for starting measurement through the operating panel 207 while the Doppler spectrum targeted for measurement is displayed. Processing in the steps S21 and S22 is manually operated.

Hereinafter, auto calculating processing is performed. That is, the tracing of the frequency that meets a predetermined condition by the trace calculating section 201 (step S23), identification of parameter points such as PSV and EDV by the index calculating section 202 (step S24), heart beat identification of an object targeted for measurement by the heart beat identifying and calculating section 203 (step S25), and index calculation by the index calculating section 204 (step S26) are sequentially executed. Then, the various calculating processing results are displayed, indexes are outputted to the display unit to be displayed on a Doppler image (step S27), whereby measurement operation terminates.

Therefore, in measurement operation of the present invention, two steps of ROI specifications (1) and (2) (refer to FIG. 3A) in the case of the conventional operation can be eliminated. Thus, the operation quantity and operation time can be significantly reduced, and examination throughput can be improved.

In addition, the measurement range can be marked or the color of the trace curve can be changed. Thus, during real-time auto tracing, the measurement range is clearly displayed, and the measurement results are easily grasped.

In the illustrative embodiment, although the trace results, PSV, and EDV are displayed for a targeted heart beat, the entire display Doppler spectrum may be displayed. In this case, it is possible to discriminate a targeted heart beat by processing such as changing a display color.

The ROI display may be set to non-display after the completion of measurement. In this case, when an image memory restarts reproduction by trackball operation, the ROI may be displayed again.

Figure 7:
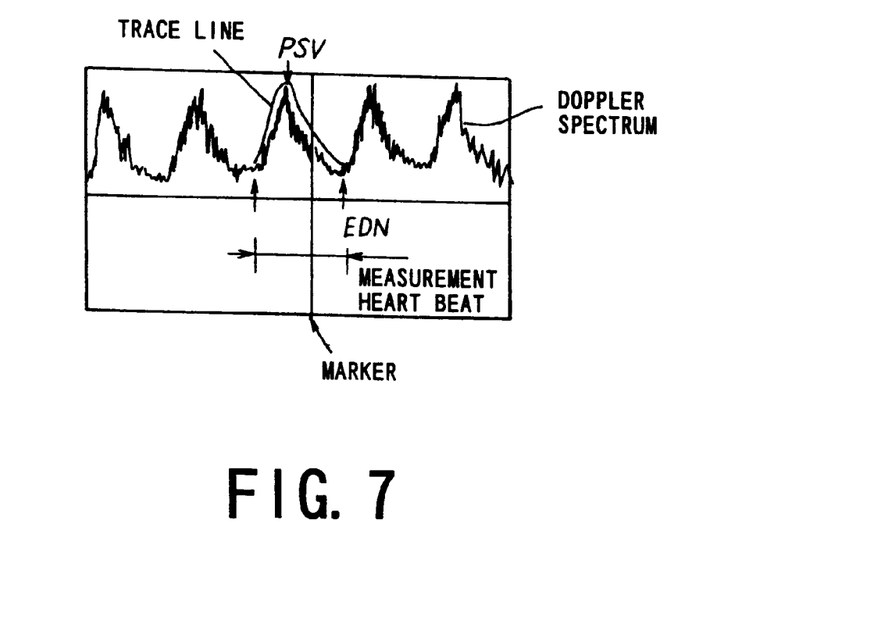
FIG. 7 is a schematic graph depicting a display example when a linear marker is employed according to the present invention.

The ROI shape may not be limited to a box shape. For example, an example when a linear marker is employed is shown in FIG. 7. In this case, the dosest systolic maximum velocity point to the linear marker position is employed for identifying a heart beat, whereby making it possible to determine a reference heart beat. Hereinafter, a heart beat component in which the reference heart beat thus determined is mainly preset can be processed as an object targeted for measurement.

The ROI is not required to be specified in advance. After the freeze memory has been reproduced, the ROI may be specified. In this case also, the time position of the closest diastolic minimum velocity point to the linear market position is detected without strict position specification, whereby a heart beat can be determined, thus making it possible to reduce operation.

Therefore, by utilizing a function for detecting the EDV and PSV of the heart cycle of a heart beat from the waveform tracing results, the heart beat (for example, the end diastole point on both sides it a peak point is included) in an approximate ROI (wave specification ROI) is detected, enabling measurement for the heart beat.

In addition, it is unnecessary to start auto calculation in step S23 or subsequent by an instruction for starting measurement. In the case where a memory reproduction work is not performed for a predetermined time, the processing in step S23 or subsequent may be performed serially.

Figure 8:
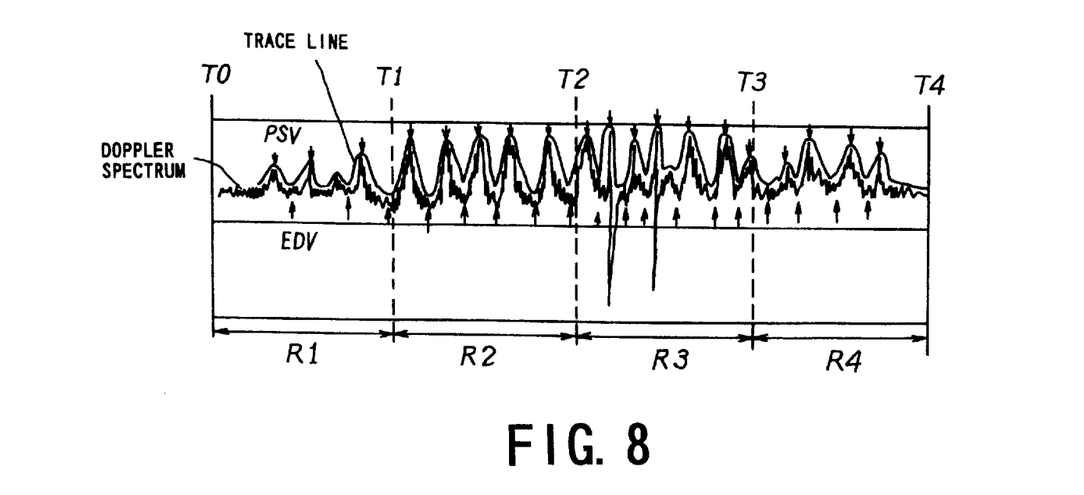
FIG. 8 is a schematic graph depicting a display example of the trace results relevant to the entire display Doppler spectrum, PSV, and EDV according to the present invention.

Further, in the case of real-time tracing, information on the trace results (trace line), PSV, and EDV (its position is indicated by arrow or the like in the figure) can be added to the Doppler spectrum data after freeze, as shown in FIG. 8, based on the output results at the trace calculating section 201 and index calculating section 202. In this case, two steps of tracing a frequency during auto calculation in FIG. 3B (step S23) and identifying a parameter point (step S24) can be eliminated, and the calculation speed is improved more significantly. In addition, there is an advantage for the operator that the operation quantity is further reduced because operational information is increased by ROI specification due to memory reproduction.

Figure 9:
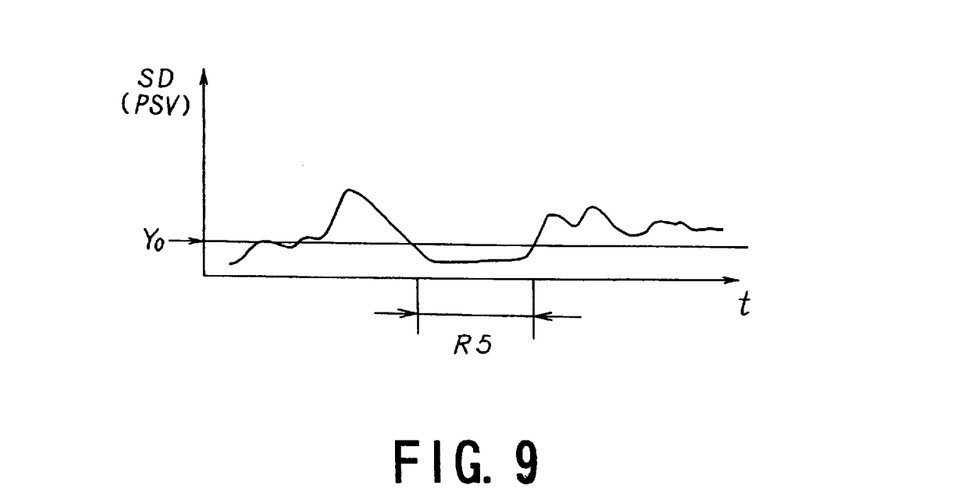
FIG. 9 is a schematic graph depicting a display example of the time change of SD of PSV according to the present invention.

In addition, in the case of real-time tracing, the output results of the time change calculating section 204 can be numerically or graphically represented on the Doppler screen in real time. FIG. 9 illustrates an example of graphically representing the standard deviation (SD) in PSV of the determined number of the past heart beat outputted from the index calculating section 202 when a time is defined on a horizontal axis. In region R5 in this graph, in comparison with another region, it is found that the SD indicates a low value, and the PSV value is stable. That is, in this case, it is easily expected that the aforementioned Doppler spectrum of the stable pattern represented by the region R2 of FIG. 4 described above is acquired. In such a case, the display color of the trace curve is changed, whereby the change of the value can be grasped. Based on this information, such change is reflected on freeze operation or the like, whereby the operation quantity can be reduced more significantly. In addition, in the case where the state of the region R5 occurs, freeze operation can be performed automatically.

In the above-described embodiment, although each calculating section for processing an image signal is structured by employing software, of course, such each calculating section may be structured of a circuit (hardware) such as digital circuit having its respective functions.

Further, in the above-described embodiment, although there is described that heart beat recognizing means for automatically recognizing the heart beat range in the Doppler spectrum is based on information on characteristic point in time change of the frequency that meets a predetermined condition in the Doppler spectrum, the present invention is not always limited thereto. An example is shown in FIG. 10 and FIG. 11.

Figure 10:
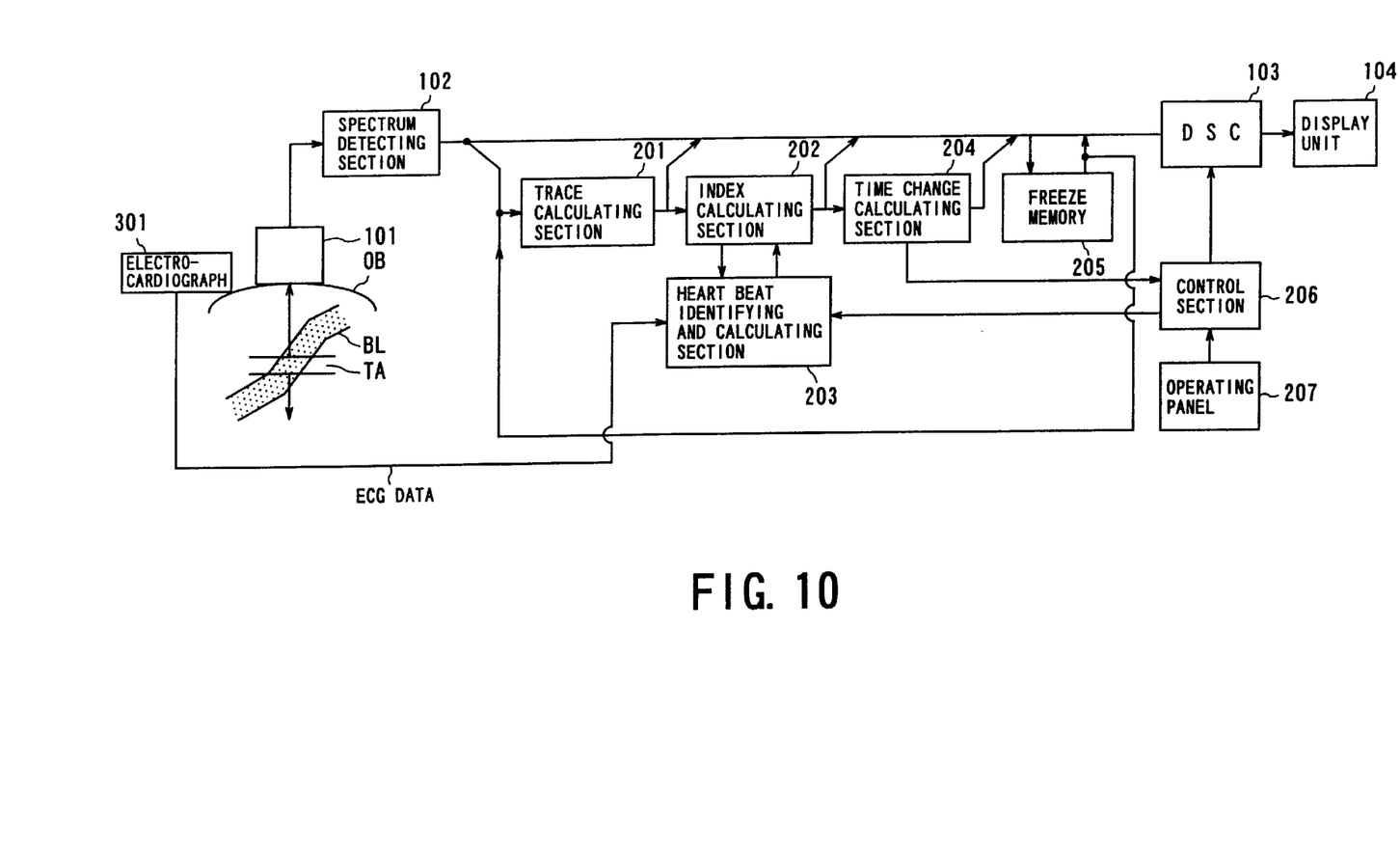
FIG. 10 is a schematic block diagram depicting an arrangement of the apparatus when a heart beat range is automatically recognized by employing ECG according to the present invention.
Figure 11:
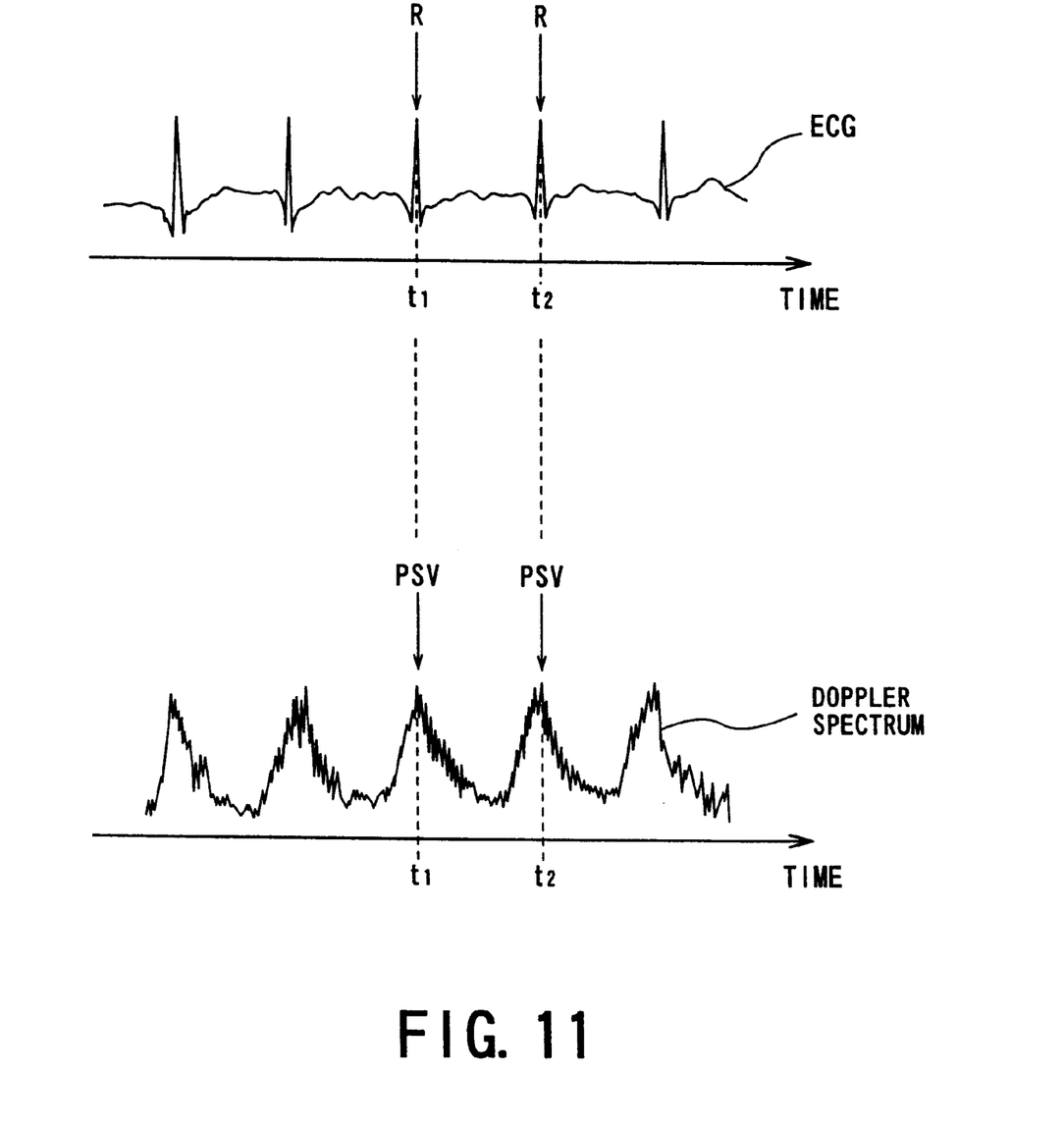
FIG. 11 is a schematic graph illustrating a function of the heart beat identifying and calculating section in the arrangement shown in FIG. 10.

In addition to an arrangement similar to the above, the Doppler ultrasonic diagnosis apparatus shown in FIG. 10 adds an electrocardiograph 301 for measuring data on the electrocardiogram (ECG) of the object's body and supplying the ECG data to the heart beat identifying and calculating section 203. In this example, as shown in FIG. 11, in addition to a function similar to the above, the heart beat identifying and calculating section 203 further comprises a function for automatically recognizing the heart beat range (for example, PSV—PSV interval) in the Doppler spectrum by employing the ECG data acquired by the electrocardiograph 301 (for example, times t1 and t2 obtained with the R—R intervals). In this manner, an advantage effect similar to the above can be achieved.

What is claimed is:

1. A Doppler ultrasonic diagnosis apparatus comprising:
   transmitting and receiving means for transmitting ultrasonic beams to diagnosis sites including motion fluid in an object to be diagnosed and receiving ultrasonic echoes thereof;
   image generating means for measuring a spectrum every moment of a Doppler signal in an ultrasonic Doppler effect due to the motion fluid based on the ultrasonic echoes received by said transmitting and receiving means, and generating a display image of said spectrum;
   selecting means for selecting a Doppler spectrum targeted for measurement from the display image generated by said display image generating means;
   heart beat recognizing means for automatically recognizing a heart beat range in said Doppler spectrum selected by said selecting means; and
   measurement means for measuring an index value for Doppler diagnosis in the heart beat range recognized by said heart beat recognizing means.

2. The Doppler ultrasonic diagnosis apparatus of claim 1, wherein said heart beat recognizing means is means for automatically recognizing a heart beat range based on information on characteristic point in time change of a frequency that meets a predetermined condition in the Doppler spectrum selected by said selecting means.

3. The Doppler ultrasonic diagnosis apparatus of claim 2, wherein said heart beat recognizing means is means for comparing a position of said characteristic point and a position of ROI preset on the display image generated by said display image generating means, and thereby automatically recognizing a heart beat range having a parameter within the range of ROI based on the comparison results.

4. The Doppler ultrasonic diagnosis apparatus of claim 3, wherein said heart beat recognizing means is means for scrolling said Doppler spectrum according to the ROI preset on said display image, thereby automatically recognizing the heart beat range having the characteristic point within the range of said ROI.

5. The Doppler ultrasonic diagnosis apparatus of claim 1, wherein said measuring means comprises:
   detecting means for detecting the frequency that meets a predetermined condition from the Doppler spectrum;
   extracting means for extracting a position of a characteristic point and its value based on a time change of the frequency detected by said detecting means;
   heart beat identifying means for identifying a heart beat range based on a position of the characteristic point and its value extracted by said extracting means; and
   calculating means for calculating an index value for Doppler diagnosis in the heart beat range identified by said heart beat identifying means.

6. The Doppler ultrasonic diagnosis apparatus of claim 5, further comprising means for measuring a time change of the index calculated by said calculating means every said heart beat.

7. The Doppler ultrasonic diagnosis apparatus of claim 1, wherein said heart beat recognizing means comprises:

electrocardiogram acquiring means for acquiring an electrocardiogram of the object in synchronism with transmission and reception of said ultrasonic beams to/from said object together With said transmitting and receiving means; and means for automatically recognizing a heart beat range in the Doppler spectrum by employing the electrocardiogram acquired by said electrocardiogram acquiring means.

8. The Doppler ultrasonic diagnosis apparatus of claim 1, further comprising:

extracting means for automatically tracing a frequency that meets a predetermined condition of the Doppler spectrum from the display image generated by said display image generating means, thereby extracting a position of the characteristic point and its value for heart beat identification based on a time change of the frequency; and measuring means for calculating a diagnosis index value based on a position of the characteristics point and its value extracted by this extracting means, thereby measuring a time change of the index value.

9. The Doppler ultrasonic diagnosis apparatus of claim 8, further comprising means for graphically representing the measurement result obtained by said measuring means on said display image.

10. The Doppler ultrasonic diagnosis apparatus comprising:

transmitting and receiving means for transmitting ultrasonic beams to diagnosis sites including motion fluid in the object to be diagnosed and receiving ultrasonic echoes thereof;

display image generating means for measuring a spectrum every moment of a Doppler signal in an ultrasonic Doppler effect due to the motion of the motion fluid based on the ultrasonic echoes received by said transmitting and receiving means and thereby generating a display image of the Doppler spectrum;

extracting means for automatically tracing a frequency that meets a predetermined condition of the Doppler spectrum from a display image generated by said display image generating means, thereby extracting a position of a characteristic point and its value for the heart beat identification based on a time change of the frequency; and measuring means for calculating a diagnosis index value based on a position of the characteristic point and its value extracted by said extracting means, thereby measuring a time change of the index value.

11. The Doppler ultrasonic diagnosis apparatus of claim 10, further comprising means for graphically representing the measurement result obtained by said measuring means on said display image.

* * * * *